US00PP24119P3

(12) United States Plant Patent
Kardos

(10) Patent No.: US PP24,119 P3
(45) Date of Patent: Dec. 31, 2013

(54) ***LANTANA* PLANT NAMED 'APRICOT SUNRISE'**

(50) Latin Name: ***Lantana* sp.**
Varietal Denomination: Apricot Sunrise

(75) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 119 days.

(21) Appl. No.: 13/374,633

(22) Filed: Jan. 4, 2012

(65) Prior Publication Data

US 2013/0174306 P1 Jul. 4, 2013

(51) Int. Cl.
*A01H 5/00* (2006.01)

(52) U.S. Cl.
USPC ..... Plt./227

(58) Field of Classification Search
USPC ..... Plt./227
See application file for complete search history.

(56) References Cited

U.S. PATENT DOCUMENTS

| | | | | |
|---|---|---|---|---|
| PP19,358 | P2 * | 10/2008 | Trees | Plt./227 |
| PP19,548 | P2 | 12/2008 | Dirr | |
| PP21,539 | P3 | 11/2010 | Griffith | |
| 2012/0084892 | P1 | 4/2012 | Kardos | |

OTHER PUBLICATIONS

*Lantana* Catalog Page (distributed at a trade show Jan. 5, 2011) "*Lantana* 'Apricot Sunrise'", 1 pg.
Plant Introductions, Inc. webpage, (downloaded Dec. 30, 2011) "*Lantana* selections", http://www.plantintroductions.com/lantanaselections.html, 3 pgs.

* cited by examiner

*Primary Examiner* — June Hwu
(74) *Attorney, Agent, or Firm* — Lathrop & Gage LLP

(57) ABSTRACT

A new and distinct cultivar of *Lantana* plant named 'Apricot Sunrise', characterized by its low growing, spreading growth habit; leathery, scabrous medium green foliage; continuous flowering; and yellow flower buds that open to yellow with a darker yellow-orange center and age to apricot pink with an orange center.

2 Drawing Sheets

Genus and species of plant claimed: *Lantana* sp.
Variety denomination: 'Apricot Sunrise'.

BACKGROUND OF THE INVENTION

The present invention relates to a new and distinct cultivar of *Lantana* plant, botanically known as *Lantana* sp., and hereinafter referred to by the cultivar name 'Apricot Sunrise'.

The new *Lantana* plant originated from a controlled cross between *Lantana* sp. 'Chapel Hill Gold' (U.S. Plant Pat. No. 21,539) and an unnamed seedling of *Lantana camara* known to the inventor as *Lantana camara* DIO (not patented) as part of a planned breeding program to develop low growing, continuously flowering *lantanas* with dark green foliage. The cultivar 'Apricot Sunrise' originated and was discovered in a cultivated environment in a greenhouse in Watkinsville, Ga.

Asexual reproduction of the new cultivar by stem cuttings in Watkinsville, Ga. has shown that all the unique features of this new *Lantana,* as herein described, are stable and reproduced true-to-type through successive generations of such asexual propagation.

SUMMARY OF THE INVENTION

Plants of the new cultivar 'Apricot Sunrise' have not been observed under all possible environmental conditions. The phenotype may vary somewhat with changes in light, temperature, soil and rainfall without, however, any variance in genotype.

The following traits have been repeatedly observed and are determined to be unique characteristics of 'Apricot Sunrise'. These characteristics in combination distinguish 'Apricot Sunrise' as a new and distinct cultivar: 1. Low growing, spreading growth habit; 2. Leathery, scabrous medium green foliage; 3. Continuous flowering; and 4. Yellow flower buds that open to yellow with a darker yellow-orange center and age to apricot pink with an orange center. There are no other cultivars of *Lantana* with this combination of characteristics known to the inventor.

Plants of the new *Lantana* 'Apricot Sunrise' differ from plants of the female parent, 'Chapel Hill Gold', primarily in flower color and foliage color, as plants of 'Chapel Hill Gold' have bright golden yellow flower buds and flowers and dark green foliage, whereas plants of 'Apricot Sunrise' have yellow flower buds that open to yellow with a darker yellow-orange center and age to apricot pink with a orange center and medium green foliage. Plants of the new *Lantana* 'Apricot Sunrise' differ from plants of the male parent, an unnamed seedling known to the inventor as *Lantana* DIO, primarily in flower color, foliage color, and growth habit, as plants of the male parent have flowers that remain light orange, dark green foliage, and a loose, rounded growth habit, whereas plants of 'Apricot Sunrise' have yellow flower buds that open to yellow with a darker yellow-orange center and age to apricot pink with a orange center, medium green foliage, and an overall wider, lower, spreading growth habit.

'Apricot Sunrise' can be compared to the cultivar 'Balandimpea' (U.S. Plant Pat. No. 19,358), but differs in the growth habit, foliage, and floral characteristics. 'Apricot Sunrise' has a low growing, spreading growth habit, whereas 'Balandimpea' has a moderately vigorous, semi-upright growth habit. 'Apricot Sunrise' has smaller, medium green mature foliage, whereas 'Balandimpea' has larger, darker green mature foliage. 'Apricot Sunrise' has mature flowers that are apricot pink with an orange center, whereas 'Balandimpea' has mature flowers that are peach-colored.

BRIEF DESCRIPTION OF THE DRAWINGS

The accompanying color photographs illustrate the flower and foliage characteristics and the overall appearance of the new *Lantana,* showing the colors as true as it is reasonably possible to obtain in color reproductions of this type. Colors in the photographs may differ slightly from the color values cited in the detailed botanical description which accurately describe the colors of the new *Lantana.*

DETAILED DESCRIPTION

Figure 1:
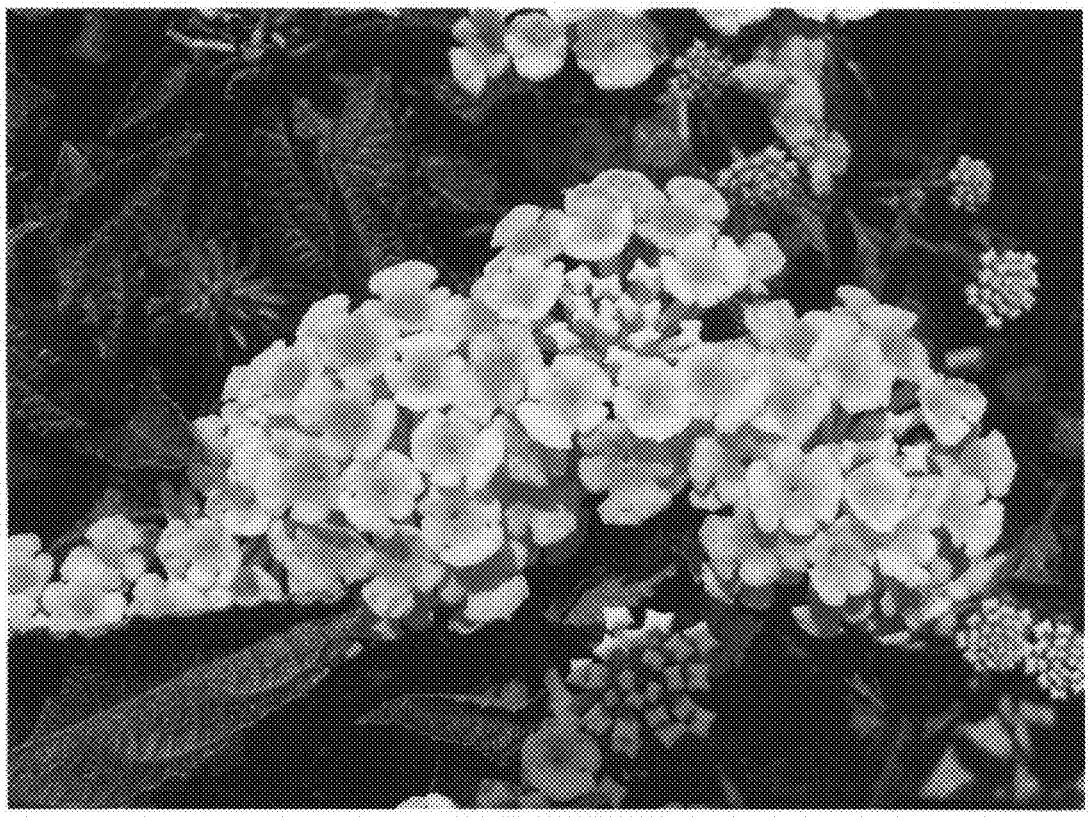
FIG. 1 illustrates a close-up view of the inflorescences and foliage of 'Apricot Sunrise'.
Figure 2:
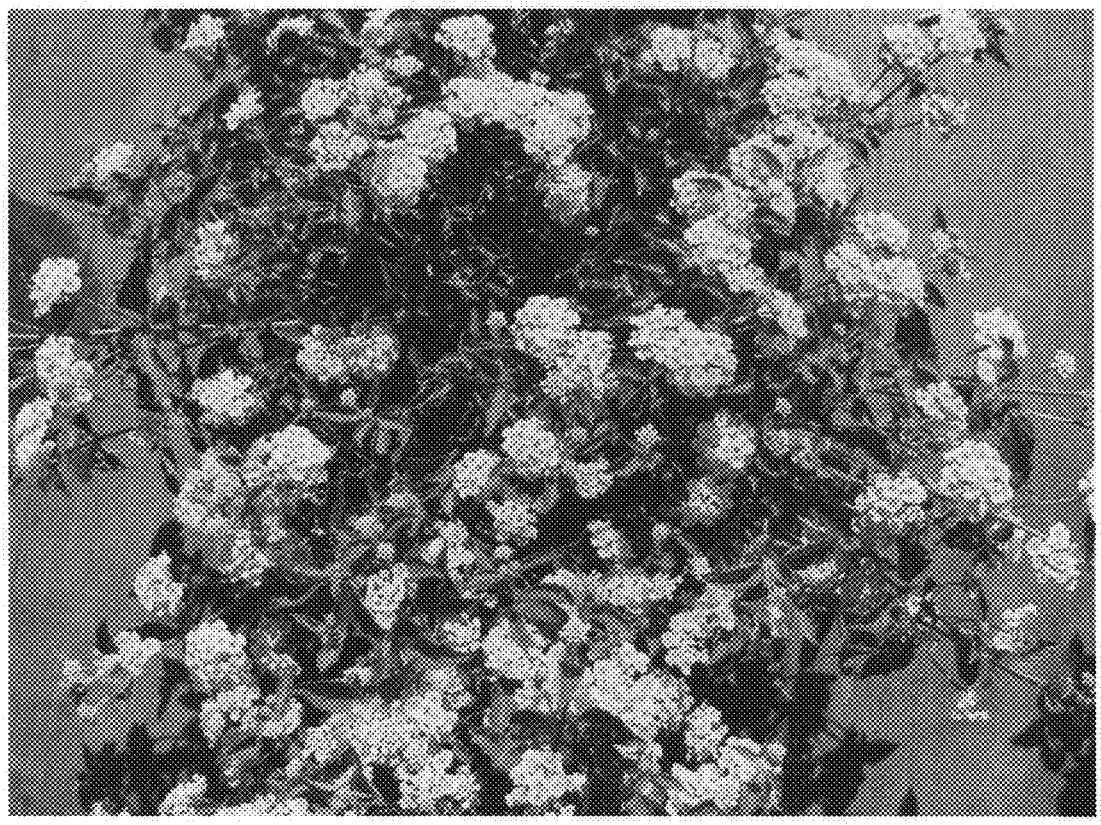
FIG. 2 illustrates the overall appearance of a mature plant of 'Apricot Sunrise' in a container.

In the following description, color references are made to The Royal Horticultural Society Colour Chart, 2001 Edition, except where general terms of ordinary dictionary significance are used. Plants used for the description were approximately six months old and were grown in 11.8 L containers in full sun under outdoor conditions in a nursery in Watkinsville, Ga.

Botanical classification: *Lantana* sp., cultivar 'Apricot Sunrise'.

Parentage:

- *Female parent.*—*Lantana* sp. cultivar 'Chapel Hill Gold' (U.S. Plant Pat. No. 21,539).
- *Male parent.*—*Lantana camara* unnamed seedling known to the inventor as *Lantana camara* DIO (not patented).

Propagation: Stem cuttings.

Time to initiate roots, summer: About 10 days at 32° C.

Plant description: Herbaceous flowering plant, subshrub, low growing, spreading growth habit. Freely branching; two lateral branches potentially forming at every node; pinching enhances lateral branch development.

- *Root description.*—Numerous, fine, fibrous and well-branched.
- *Plant size.*—About 41 cm in height from the soil level to the top of the inflorescences, and about 125 cm in diameter. Young stems having a diameter of about 3 mm and a squarish shape. Mature stems having a diameter of about 4 mm or more and a rounded shape.
- *Stem strength.*—Strong, but flexible.
- *Stem texture.*—Coarse, pubescent.
- *Stem color* (*young*).—146C. Color (mature): 199B.
- *Internode length.*—About 2 cm.

Vegetative buds: Opposite in arrangement, valvate, ovoid, pubescent.

- *Color.*—146C.
- *Size.*—About 1 mm in length and about 1 mm in width.

Foliage description:

- *Arrangement.*—Opposite, simple.
- *Length.*—About 4 cm.
- *Width.*—About 2.2 cm.
- *Shape.*—Ovate.
- *Apex.*—Acute.
- *Base.*—Cuneate.
- *Margin.*—Crenate, slightly cupped.
- *Texture* (*upper surface*).—Leathery, moderately waxy, with scabrous pubescence.
- *Texture* (*lower surface*).—Rough, with hispid pubescence.
- *Venation pattern.*—Pinnate.
- *Venation color* (*upper surface*).—144B.
- *Venation color* (*lower surface*).—145A.
- *Fragrance.*—Pungent, mint-like.
- *Color of developing foliage* (*upper surface*).—146A.
- *Color of developing foliage* (*lower surface*).—147B.
- *Color of mature foliage* (*upper surface*).—147A.
- *Color of mature* (*lower surface*).—147B.
- *Petiole length.*—About 6 mm.
- *Petiole diameter.*—About 2 mm.
- *Petiole texture, both surfaces.*—Hispid pubescence.
- *Petiole color* (*upper and lower surfaces*).—146C.

Flower description:

- *Flower type and habit.*—Small salverform flowers arranged in axillary corymbs; flowers face mostly upward or outward. Flowers are self-cleaning. Freely flowering with potentially two inflorescences per node; typically about 20 to 25 flowers per corymb.
- *Natural flowering season.*—Spring until the first frost in fall; flowering is continuous. Flower longevity on the plant: about one week. Fragrance: none observed.
- *Inflorescence diameter.*—About 3.7 cm.
- *Inflorescence height.*—About 1.8 cm.
- *Flower bud length.*—About 1 cm.
- *Flower bud diameter.*—About 3 mm.
- *Flower bud shape.*—Oblong.
- *Flower bud color.*—13C.
- *Flower appearance.*—Flared trumpet, corolla fused, four-parted; flowers roughly rectangular in shape.
- *Diameter.*—About 1.1 cm.
- *Corolla tube length.*—About 1.1 cm.
- *Pedicels.*—None observed, flowers not stalked.

Petals:

- *Arrangement/appearance.*—Single whorl of four petals, fused into flared trumpet.
- *Petal length from throat.*—About 6 mm for the upper petal, about 4 mm for the lower petal, and about 4 mm for the lateral petals.
- *Petal width.*—Upper and lower petals are about 7 mm in width, and lateral petals are about 4 mm in width.
- *Petal shape.*—Spatulate to somewhat orbicular.
- *Petal apex.*—Obtuse.
- *Petal base.*—Fused.
- *Petal margin.*—Entire.
- *Petal texture, upper and lower surfaces.*—Smooth, glabrous.
- *Petal color* (*young*).—Upper surface: 13C and lower surface: 11C. Color of center: 14B. Color of corolla tube: 12C.
- *Petal color* (*mature*).—Upper surface: 35C and lower surface 36B. Color of center: 28A. Color of corolla tube: 36B.

Calyx:

- *Arrangement/appearance.*—The calyx consists of 5 sepals fused into a single tubular structure. Length is about 5 mm. Width is about 2 mm.
- *Sepal base.*—Fused.
- *Sepal apex.*—Acute.

*Texture, upper and lower surfaces.*—Scabrous.
*Color, upper and lower surfaces.*—144A.

Bracts:
*Arrangement/appearance.*—One bract per flower at the base of the corolla, leaf-like. Length is about 6 mm. Width is about 1.5 mm.
*Shape.*—Lanceolate.
*Apex.*—Acute.
*Margin.*—Entire.
*Texture, upper and lower surface.*—Scabrous.
*Color, upper and lower surfaces.*—144A.

Peduncles:
*Length.*—About 4 cm.
*Diameter.*—About 1.5 mm.
*Angle.*—About 45 degrees from the stem.
*Strength.*—Flexible, but strong.
*Color.*—146C.

Stamens:
*Quantity/arrangement.*—Four per flower, adnate to the inside of the corolla tube.
*Anther shape.*—Oblong.
*Anther length.*—1 mm.
*Anther width.*—Less than 1 mm.
*Anther color.*—13B.
*Pollen amount.*—Produced in very small quantities, and 13B in color.

Pistils:
*Quantity.*—One inferior pistil per flower.
*Pistil length.*—About 4 mm.
*Stigma shape.*—Rounded.
*Stigma size.*—About 1 mm in diameter.
*Stigma color.*—145C.
*Style length.*—About 2 mm.
*Style color.*—145D.
*Ovary size.*—About 1 mm in diameter.
*Ovary color.*—145A.

Fruit:
*Type/appearance.*—Drupe.
*Shape.*—Round.
*Diameter.*—About 5 mm.
*Mature color.*—202A.
*Number per infructescence.*—Ranges from zero to about five.

Disease/pest resistance: Plants of the claimed *Lantana* variety grown in the garden have not been noted to be susceptible or resistant to pathogens and pests common to *Lantana*.

Weather and temperature tolerance: Plants of the new variety have been observed to be cold hardy to U.S. Cold Hardiness Zone 8.

I claim:

1. A new and distinct *Lantana* plant named 'Apricot Sunrise', as illustrated and described herein.

* * * * *